United States Patent [19]
Owens

[11] Patent Number: 5,065,083
[45] Date of Patent: Nov. 12, 1991

[54] MICROPROCESSOR CONTROLLED ELECTRONIC STIMULATING DEVICE HAVING A BATTERY MANAGEMENT SYSTEM AND METHOD THEREFOR

[75] Inventor: Alan R. Owens, Longmont, Colo.
[73] Assignee: Staodyn, Inc., Longmont, Colo.
[21] Appl. No.: 398,745
[22] Filed: Aug. 25, 1989
[51] Int. Cl.[5] .......................... H02J 7/00; A61N 1/00
[52] U.S. Cl. ....................................... 320/13; 320/48; 320/37; 340/636; 128/421
[58] Field of Search ...................... 320/13, 14, 37, 48; 307/66; 340/636; 128/421

[56] References Cited
U.S. PATENT DOCUMENTS

| | | | |
|---|---|---|---|
| 3,979,657 | 9/1976 | Yorksie | 320/13 |
| 4,380,726 | 4/1983 | Sado et al. | 320/37 X |
| 4,632,117 | 12/1986 | James | 128/421 |
| 4,703,247 | 10/1987 | Morioka | 320/13 |
| 4,726,052 | 2/1988 | Kato et al. | 320/13 X |
| 4,908,523 | 3/1990 | Snowden et al. | 307/66 X |

Primary Examiner—R. J. Hickey
Attorney, Agent, or Firm—Robert E. Harris

[57] ABSTRACT

A device and method are disclosed for effecting battery management in a battery powered electronic stimulating device, with the stimulating device particularly illustrated being a transcutaneous nerve stimulating (TENS) device for effecting suppression of pain by nerve fiber stimulation. The output power is in the form of biphasic constant current output pulses generated at one or more biphasic output stages. Each output stage receives high voltage, derived from the battery, along with microprocessor generated control pulses. Battery management is effected by detecting predetermined voltage levels and responsive thereto decrementing the output power to maintain the battery voltage at a selected lower level with termination of operation occurring when such decrementing can no longer maintain the lower battery voltage. A battery warning indicator is also provided for advising of battery condition.

19 Claims, 10 Drawing Sheets

Fig_1

Fig_2

Fig_3

Fig_4A

Fig _4B

Fig_4C

Fig_5A

Fig_5B

Fig_6A

Fig_6B

Fig_7A

Fig_7B

MICROPROCESSOR CONTROLLED ELECTRONIC STIMULATING DEVICE HAVING A BATTERY MANAGEMENT SYSTEM AND METHOD THEREFOR

FIELD OF THE INVENTION

This invention relates to an electronic stimulating device, and, more particularly, relates to a device and method for effecting battery management in a battery powered electronic stimulation device such as a transcutaneous nerve stimulating (TENS) device.

BACKGROUND OF THE INVENTION

The use of electronic stimulating devices are now well known, and examples of such devices to suppress pain are also now well known (see, for example, in U.S. Pat. Nos. 4,014,347, 4,210,150 and 4,632,117).

It is also well known that such devices have heretofore commonly included fault indicators, such as visual indicators for indicating low battery voltage (see, for example, U.S. Pat. No. 4,632,117).

More recently, it has been found that biphasic pulses can be used to good advantage in connection with electronic stimulating devices, and examples of devices generating biphasic pulses are shown, for example, in U.S. Pat. Nos. 2,375,575 3,946,745, 4,237,899 and 4,256,116.

Still more recently, it has been found that specific groupings of biphasic pulses can be used to increase the activity of selected nerve fibers (see U.S. Pat. No. 4,640,286). It has also been found that specific groupings of biphasic pulses can be used to good advantage with plural equally active electrodes (see U.S. Pat. No. 4,803,988), and, more particularly, with symmetrical biphasic pulses applied through equally active electrodes to one or more channels (see U.S. Pat. No. 4,813,418).

Transcutaneous nerve stimulating devices providing dual channel isolation and including capacitively coupled outputs have also heretofore been suggested for use with monopolar-type stimulation (see, for example, U.S. Pat. No. 4,632,117 wherein a high voltage power supply is connected to the electrodes by transistor switches controlled by control pulses provided thereto by a pulse generator, with the power supply being isolated from the user by a capacitor/diode arrangement so that the device cannot directly deliver any net DC charge to the user, and with a bleeder resistor that discharges the output capacitor during the intervals between the pulses).

Microprocessor controlled transcutaneous nerve stimulating devices have also been heretofore suggested for use with transformer coupled transcutaneous nerve stimulating devices producing a biphasic pulse output (see, for example, U.S. Pat. No. 4,640,286).

Thus, while electronic stimulating devices have been heretofore suggested, and while such devices have heretofore been extensively modified, additional improvements can still be utilized to good advantage.

SUMMARY OF THE INVENTION

This invention provides an improved electronic stimulating device, such as a transcutaneous nerve stimulating (TENS) device, that includes a battery management system, together with a method for effecting battery management, and a display for indicating battery condition.

The device is battery powered and includes a control unit, preferably a microprocessor, for generating control pulses that are provided to one or more output stages, or channels, along with high voltage so that each output stage generates biphasic output pulses, which pulses are coupled from each output stage for application to a user through an electrode pair noninvasively positioned at the skin of the user, with the control unit effecting management of the battery with a view toward gaining maximum battery use.

It is therefore an object of this invention to provide an improved electronic stimulating device that includes battery management.

It is another object of this invention to provide an improved transcutaneous nerve stimulating device as the electronic stimulating device that includes battery management.

It is still another object of this invention to provide an improved electronic stimulating device that includes a microprocessor for effecting battery management.

It is still another object of this invention to provide a device and method for effecting battery management.

With these and other objects in view, which will become apparent to one skilled in the art as the description proceeds, this invention resides in the novel construction, combination, arrangement of parts, and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 2 illustrates typical control pulses provided by the microprocessor to control generation of biphasic output pulses at the dual output stages as shown in FIG. 1;

FIG. 3 illustrates typical biphasic pulse outputs coupled from the dual output stages as shown in FIG. 1;

FIGS. 4A through 4C, taken together, form a flow chart for generation of control pulses using a microprocessor as the control unit;

FIG. 5A is a simplified illustration of a capacitively coupled output stage providing a biphasic pulse output;

FIG. 5B is a schematic diagram illustrating the bleeder circuitry shown in block form in FIGURE 5A;

FIGS. 7A and 7B, taken together, form an alternative embodiment of a flow chart for microprocessor controlled management by the control unit.

DESCRIPTION OF THE INVENTION

Figure 1:
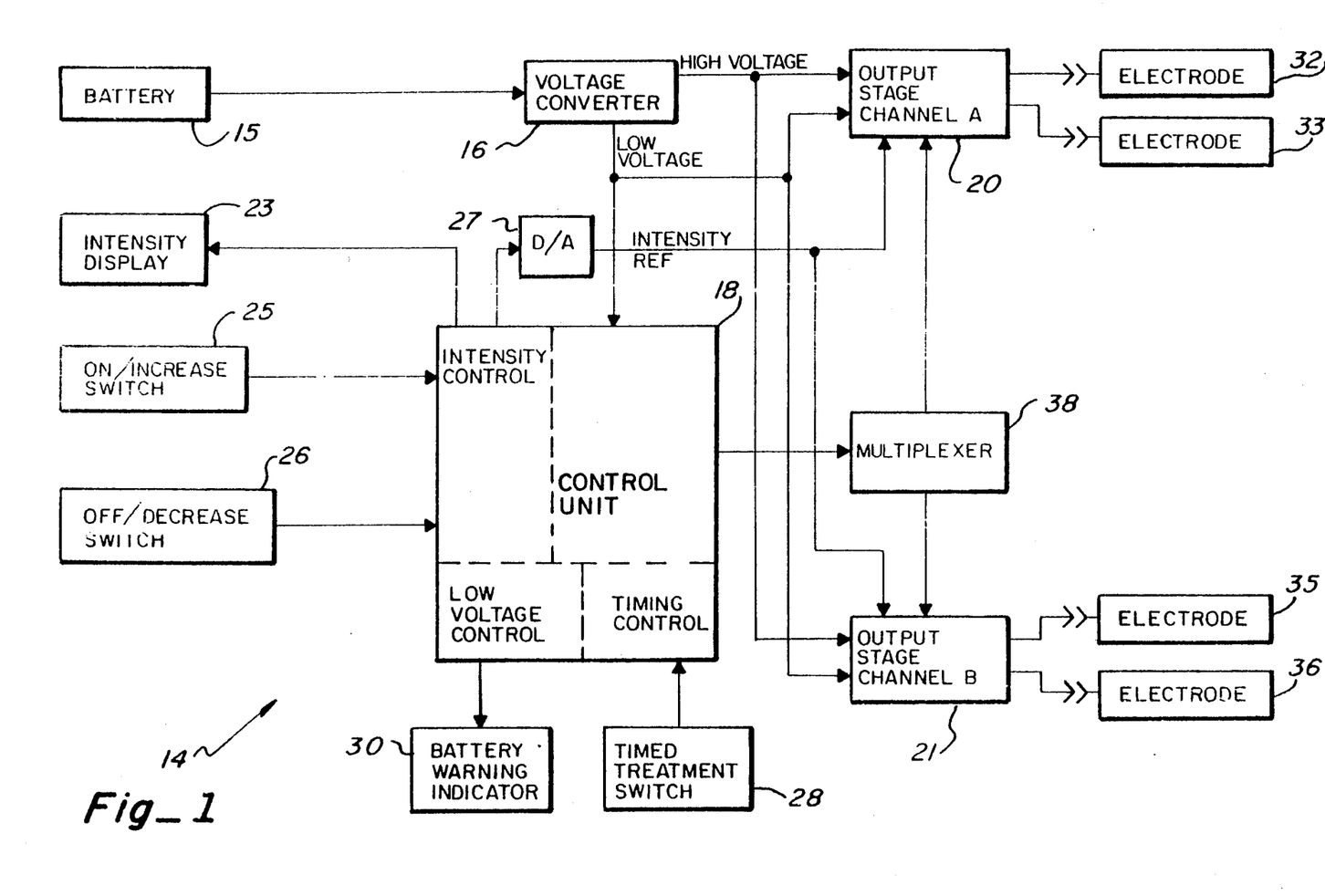
FIG. 1 is a block diagram illustrating an electronic stimulating device, which device is illustrated as a transcutaneous nerve stimulating device, and which device includes provision for effecting battery management.

An electronic stimulating device, and, more particularly, a transcutaneous nerve stimulating device 14 is shown by the block diagram of FIG. 1. As shown, battery 15 is utilized as the sole power source to power device 14. Battery 15, preferably a 9 volt battery, is connected with conventional voltage converter, or inverter, 16, and converter 16 supplies a low voltage DC output, preferably 5 volts, to microprocessor control unit 18, as well as to output stages, or channels, 20 and 21. In addition, converter 16 also supplies a high voltage DC output, preferably 100 volts maximum, to output stages 20 and 21.

Microprocessor control unit 18 has an intensity display 23 connected therewith, with the intensity being varied by intensity on/increase switch 25 and intensity off/decrease switch 26, both of which are externally actuatable. As also indicated, an intensity reference (the level of which is selected using intensity switches 25 and 26 in conjunction with the intensity control provided by control unit 18) is supplied by microprocessor control unit 18, converted to analog form in digital-to-analog (D/A) converter 27, and then coupled to output stages 20 and 21.

Microprocessor control unit 18 also provides a timing control (for use during the programmed treatment mode of operation of the device) that is activated by timed treatment switch 28. In addition, microprocessor control unit 18 provides battery management with indications relating to battery management being produced at battery warning indicator 30.

Output stage 20 (channel A, or 1, as also referred to herein) is connectable with electrodes 32 and 33, providing a first electrode pair, and output stage 21 (channel B, or 2, as also referred to herein) is connectable with electrodes 35 and 36, forming a second electrode pair.

Microprocessor control unit 18 generates control pulses, as typically shown in FIG. 2, with the control pulses designated for channel A being coupled through multiplexer 38 to output stage 20, and with the control pulses designated for channel B being coupled through multiplexer 38 to output stage 21, to control generation of the biphasic pulse outputs at each output stage, or channel, as typically shown in FIG. 3.

Figure 4B:
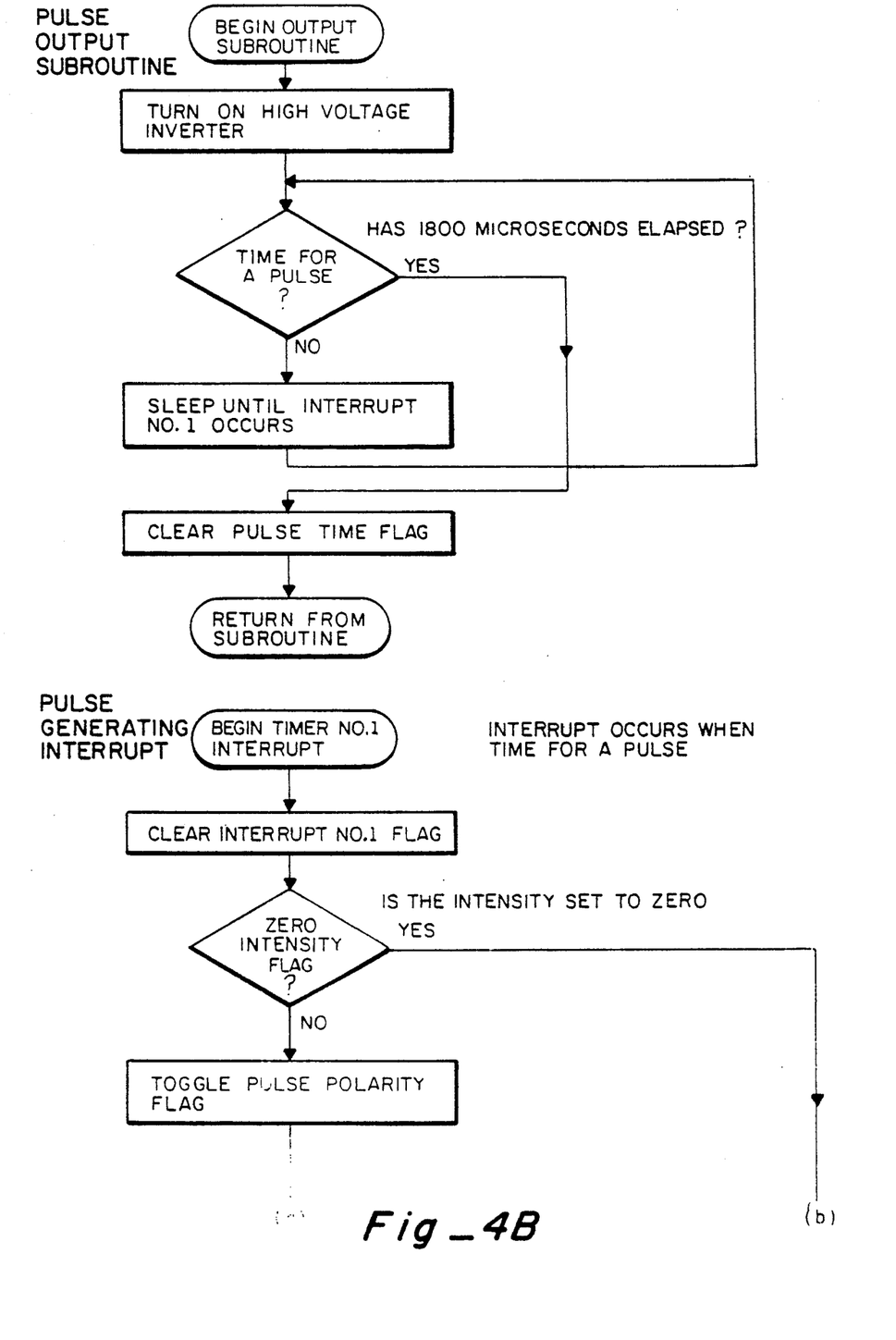
Figure 4C:
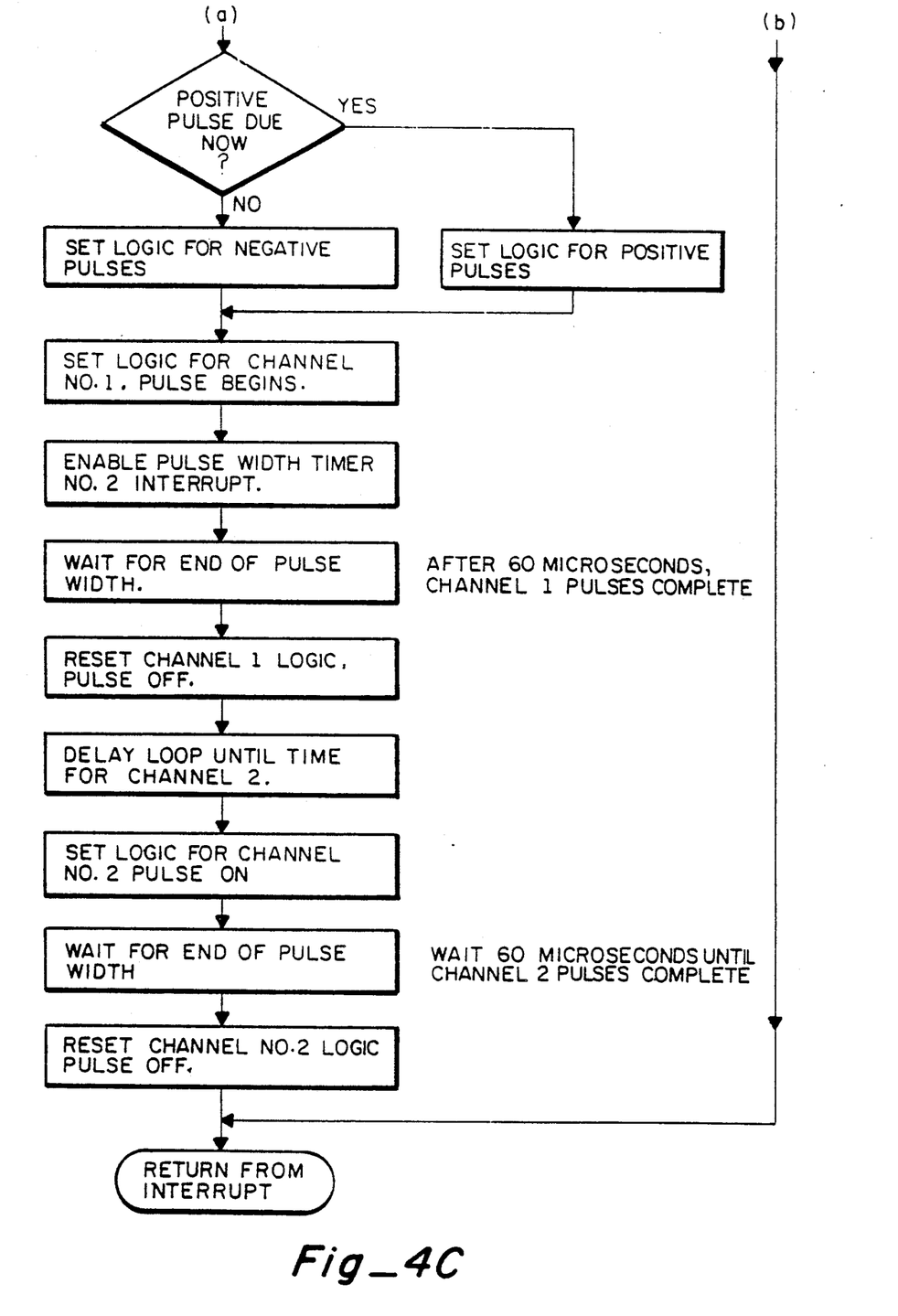

A more detailed explanation of the control pulses, as well as the biphasic pulse output to be provided, is set forth U.S. Pat. No. 4,813,418, which is hereby incorporated herein by reference. A flow chart for pulse generation using a microprocessor is shown in FIGS. 4A through 4C. While microprocessor control unit 18 is now preferred, apparatus for producing control pulses, as shown and described in U.S. Pat. No. 4,813,418 could also be utilized as the control unit.

Control unit 18, in conjunction with digital-to-analog converter 27, provides intensity control, preferably by causing a stepped output, from output stages 20 and 21.

A biphasic output stage requires circuitry that enables generation of pulses having both positive and negative polarities. As indicated by the simplified schematic diagram of FIG. 5A, this can be accomplished using four transistor switches 40, 41, 42 and 43. Switches 40 and 41 are gate on/off transistors that connect high voltage supply 45 to an electrode pair (such as, for example, by providing high voltage from converter 16 to electrodes 32 and 33, as indicated by FIG. 1) at different times. The transistors are turned-on by control pulses supplied thereto from control pulse generator 47 (which pulses can be generated, for example by microprocessor control unit 18, as indicated in FIG. 1) with the control pulses provided being as indicated, for example, in FIG. 2 (it being realized that the pulse spacing between channels could be varied, as, for example, utilizing 180 ms between occurrences of like pulses in different channels as is now preferred in some TENS devices being provided).

Switches 42 and 43 functionally include variable resistance represented in FIG. 5B as variable resistors 49 and 50 connected in series therewith and these transistors serve both as switches and current level control variable resistors. When not turned on by a control pulse, the transistors are off and have infinite resistance. When a biphasic pulse output is produced (such as shown in FIG. 3, for example), conductance is determined by a voltage reference that sets the desired level of current for the pulses. Since variable-resistor/switch transistors 42 and 43 are connected to opposite electrodes, they cannot be combined and must be separate transistors that are turned on at different times by control pulses.

Positive and negative bleeder networks, or circuits, 52 and 53 discharge any voltage that may appear across output capacitors 54 and 55 (used to capacitively couple the output pulses from the device to the associated electrodes). If the two polarities of the output stage are perfectly balanced, the pulses generated can contain precisely the same charge and there would be no need for bleeder circuits, but this, most often, does not occur.

Positive bleeder circuit 52 is shown in schematic form in FIG. 5B (negative bleeder circuit 53 is identical to positive bleeder circuit 52 and has not been specifically illustrated). As shown in FIG. 5B, positive bleeder circuit 52 includes diode 56 (connected to one side of capacitor 54), transistor 57, resistor 58, and an RC network (consisting of parallel connected resistor 59 and capacitor 60) for transistor turn-on (negative bleeder circuit 53 has the diode connected to one side of capacitor 55). Such a bleeder circuit turns on slightly whenever the voltage on the gate rises sufficiently to turn on the transistor. As soon as this voltage has charged the capacitor across the base of the bleeder transistor, the bleeder transistor will turn on sufficiently for capacitor discharge.

When two output capacitors (such as capacitors 54 and 55) are used, however, there is no complete DC path around the circuit to fully discharge the capacitors. If the capacitors become equally charged to a sufficient voltage, for example 20 volts, while circuits 52 and 53 would ensure that the voltages across these two capacitors were equal, circuits 52 and 53 could not actually dissipate the accumulated charge unless a DC path is provided.

In practice, charge sometimes gathers in these capacitors. This is important because small, compact ceramic capacitors lose their capacitance when the voltage across them is high. This causes the output pulses to have sloping top portions and even greater voltage across the capacitors. The charge problem is effectively corrected by including a high resistance shunt 62 across one of the two output capacitors, as illustrated in FIG. 5A. Only one of the output capacitors is shunted so that one capacitor remains in the output current path to ensure that the net DC delivered to the patient will be zero.

The skin of a user between spaced electrodes appears as a complex RC network which illustrates that, although the ohmic resistance path across the tissue may be high, it is nevertheless an ohmic path that can conduct DC charge around a circuit path to discharge both capacitors 54 and 55.

A bleeder circuit, such as shown in FIG. 5B, has another function. If the pulse width should become very long and/or the pulse amplitude should become very high, the bleeder circuit will turn on hard and actually short out the voltage across the two electrodes. This function serves as a safety device in the event that the logic circuitry fails and produces extremely long turn-on control pulses.

While a bleeder circuit such as illustrated in FIG. 5B can also include a diode positioned between the junction of resistor 59 and capacitor 60 and the junction of transistor 57 and electrode 33, such a diode operates, at least in part, as a clamp, and has been found to be undesirable for use with a biphasic output stage because a spike of current (handled by such a diode) will destroy the interphase delay that is necessary in the output stage.

With battery powered devices, battery rundown normally causes the power output of the device to fade along with the voltage and hence conservation of battery energy is important. Eventually, however, battery rundown will occur. Some now known electronic devices, including transcutaneous nerve stimulating devices, have regulator circuitry that will maintain the power output constant even though the battery is fading. Such regulator circuits have a limited dynamic range, however, and when the battery voltage drops below the range to be regulated, the output will drop rapidly.

In some electronic devices, including some transcutaneous nerve stimulating devices, this has not been a problem since there has been sufficient time to detect and display the low battery condition to thereby warn the user of an impending cutoff. However, cutoff occurs quickly because, as the battery voltage drops, the current drawn rises to hold the power output constant. When regulation finally fails, the drain on the battery is quite high and the battery completely fails for all practical purposes.

When microprocessor control circuits are utilized, the voltage required to run such circuits (usually 5 volts) must be carefully regulated and free from spikes. The now known integrated regulators that do this (such as, for example, the National LP 2951) also normally handle the power-on reset function.

Unfortunately, this same reset function will also reset the processor if the 5 volt supply dips too low. If this should happen, the device output will shut off abruptly. Because the current drain at shut-off is very high, the battery will quickly recover and the device will come back on, the processor will reset, and the battery may even appear to be relatively healthy since the heavy load has been removed.

However, after reset has occurred, the memory has been erased and the processor therefore has no retention of the low battery problem. If the processor performs a battery check, the voltage appears low but usable because the load on the battery is light with the power output shut off. When the user tries to resume the treatment, the voltage will fall and reset will occur again.

In addition, as switching power supplies have improved, such supplies commonly operate with lower battery voltages and the final failure of a battery occurs more abruptly.

A device exhibiting the foregoing often causes a user to become confused and can cause the user to assume the device to be unpredictable and perhaps even cause the user to lose confidence in the device to such an extent that the user will no longer use the device.

A battery management system can eliminate such confusion. Such a system, as set forth herein, first detects a low battery voltage (preferably 5.95 volts in the embodiment illustrated) at a first, or upper, voltage threshold. When so detected, a display of a warning indication is preferably displayed at indicator 30 (which indication may be effected by a flashing (or, if desired, continuous) yellow LED, but could also include a message display in lieu of, or in addition to, a visual indicator such as provided by a light such as an LED). When a low battery voltage is detected to cause a warning indication to be displayed at indicator 30, the display is preferably maintained to alert the user that the device may not be supplying the intensity selected.

Soon after a low battery voltage is detected, the battery voltage will begin to fall rapidly and the current drain will soar until a second low voltage threshold (preferably 5.54 volts in the embodiment illustrated) is reached and detected. When the second low voltage threshold is detected, the power output of the device is decremented to simulate the fading power output (that normally occurs, for example, in a simple device not equipped with regulatory circuitry) which causes the battery voltage to be maintained at the second low voltage level if, and so long as, the battery has the capability of so doing.

The situation is thus controlled by reducing the power output from the device to regulate the battery voltage and hold the battery voltage at a lower, but safe, operational level (i.e., at the second low voltage level, which level is less than normally provided by a fully charged battery). In this way, reset is prevented, and the processor retains a memory of what is occurring.

The amount of power reduction that occurs during each decrementing is quite small (0.39 ma has been found to be preferable, although a reduction of 1.0 ma has been utilized for therapeutic use such as for wound healing) compared with the overall power.

If the amplitude of the output current must be carefully maintained (as is the case for some devices) the device can be provided with an indicator to provide an indication (such as, for example, by an audible indication such as a beep, or indicator 30 could be modified to also provide a visual indication) to indicate each occurrence of power decrementing.

The device continues decrementing the output until either the treatment ends or the processor is no longer able to hold the voltage at the second low voltage level.

A third low battery level or threshold (about 5.3 volts in the embodiment illustrated) is reached after output decrementing no longer holds the voltage at the second voltage level. At this point, the output is stopped, and indicator 30 is caused to display an indication (such as by a light indication, although other types of indications, such as a message display, for example, may also be utilized) that treatment has been halted due to low battery voltage and/or that treatment resumption requires battery replacement (and/or that the device must also be reset).

The fact that the amplitude was decremented and/or treatment was halted due to low battery voltage may be recorded, if necessary or desirable. Recording, is not practical however when the 5 volt supply is low so it is important that 5 volts be available when such a recording is made.

Figure 6A:
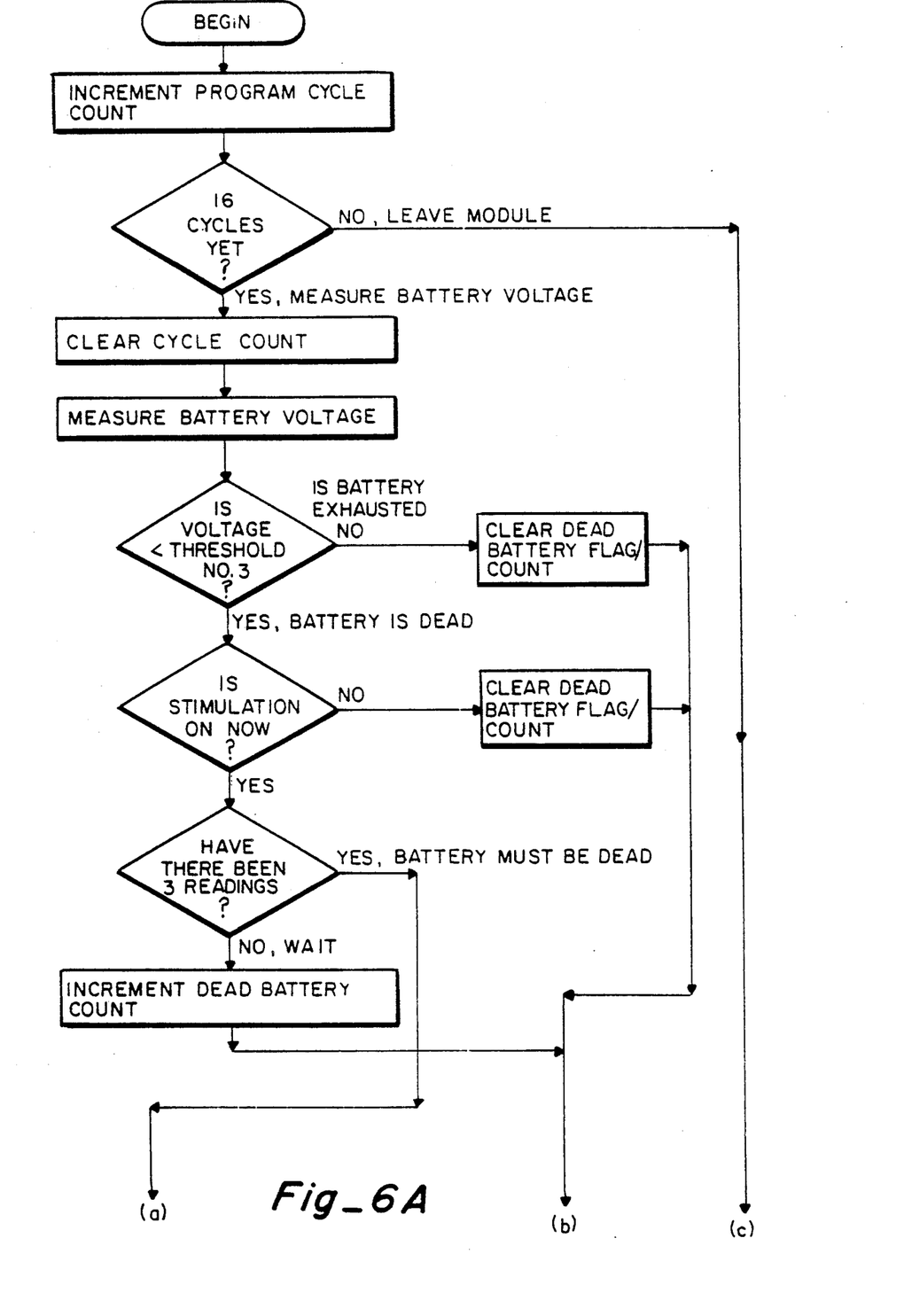
FIGS. 6A and 6B, taken together, form a flow chart for microprocessor battery management by the microprocessor control unit.
Figure 6B:
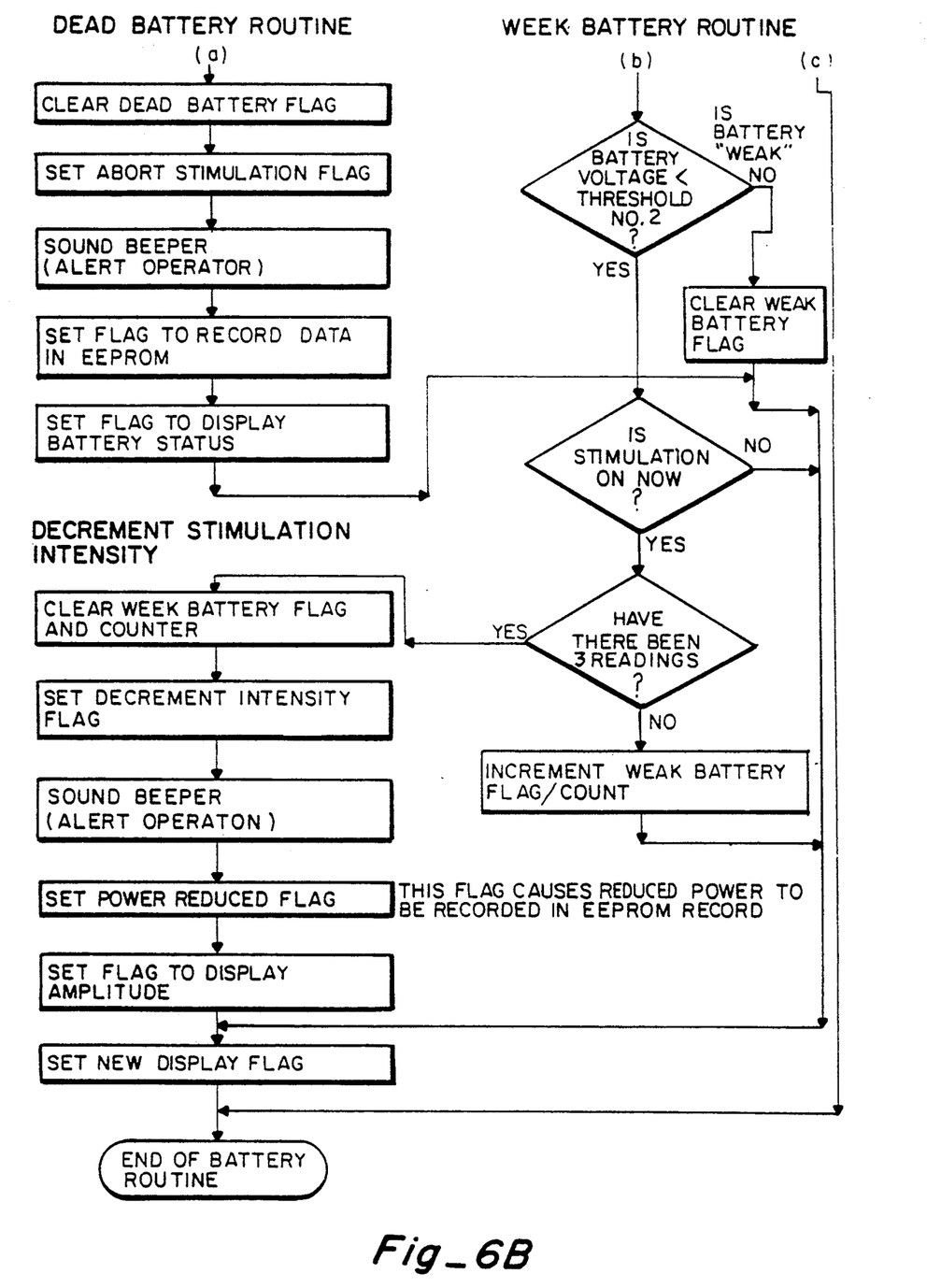

A flow chart for battery management is set forth in FIGURES 6A and 6B.

Because the battery voltage does not change instantly in response to load changes, the battery voltage need be checked only periodically. A count can be utilized to keep track of when the battery should be checked, and changes can be made, for example, every sixteen cycles of the overall program of the processor. To prevent error by the battery management system acting on false information and erroneously decrementing or terminating the power output, the capacitor is prevented from changing the then utilized mode unless the information indicating the need for change be received during the last three consecutive cycles. It has been found to be advantageous to require that a needed change indication be detected more than three times so that the "are you sure" algorithm is adequately able to average the battery voltage measurements over a sufficient period such that the unit will not change modes prematurely.

The result of use of the battery management system as set forth herein is that the low voltage threshold can be significantly lower, thereby extracting the maximum energy from the battery.

An alternative method can also be used to ensure maximum battery use while compensating for erratic battery voltage. In this algorithm, as set forth in FIGS. 7A and 7B, the output power is incremented back up toward the previous treatment level in the event that the battery should appear to recover. In other words, the battery voltage becomes fully regulated by changing the power output.

Figure 7B:
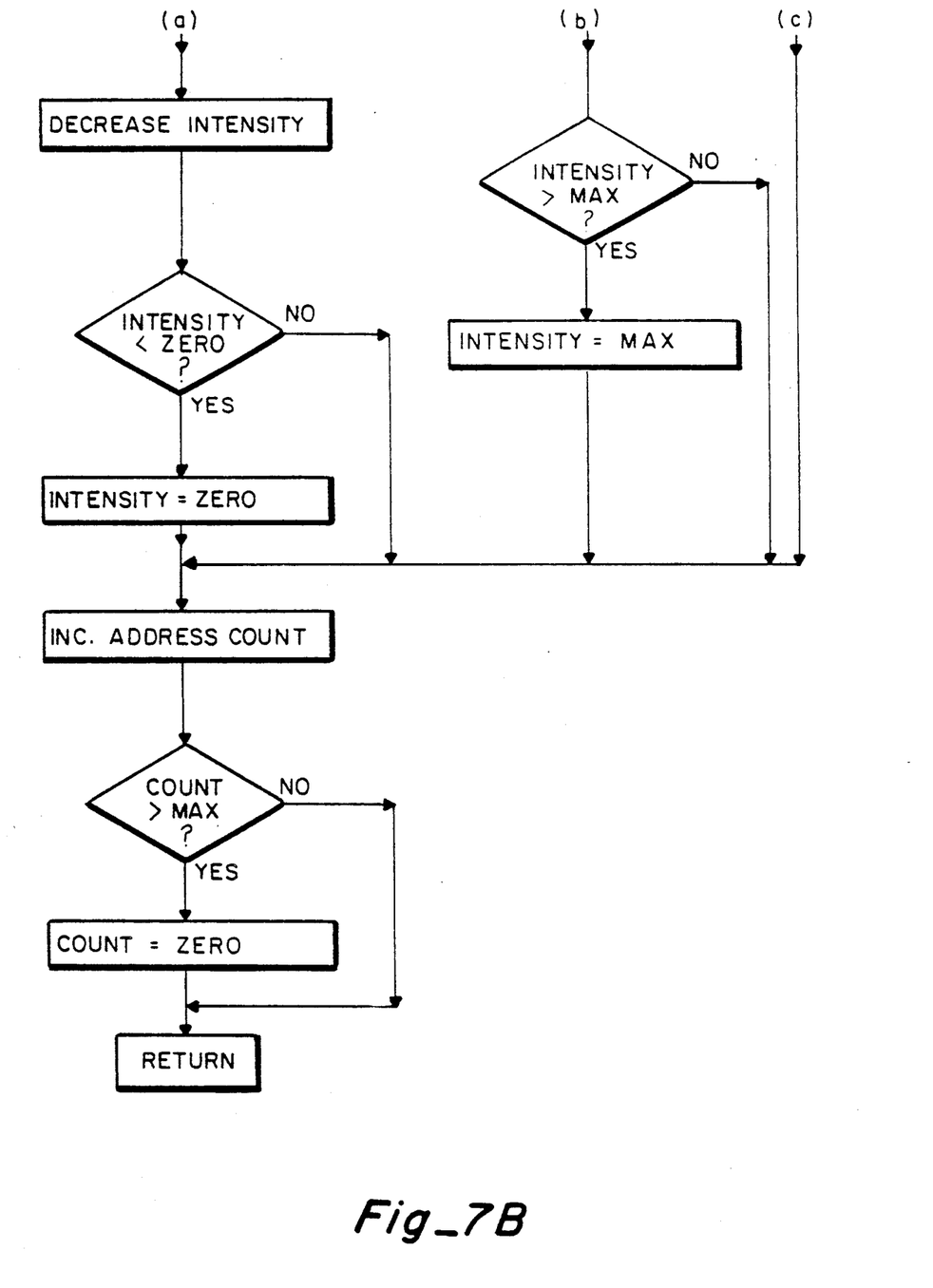

An important feature of this algorithm is that the output power setting is never incremented when the output power is off or being ramped up or ramped down. Incrementing is only allowed to occur when the output is on and the load on the battery is maximum. Typically, increments occur during the beginning of the on time, and then decrements again as the battery voltage falls.

In summary, hardware voltage regulators hold the power output constant until the battery is near exhaustion. In this battery management system, on the other hand, the output power is regulated to hold the battery voltage at preselected constant levels (with operation of the device being terminated when the hardware voltage regulators detect a low battery voltage level below that used as the low battery voltage for incrementing or decrementing the power output).

As can be appreciated from the foregoing, this invention provides an improved electronic stimulating device and, more particularly, an improved transcutaneous nerve stimulating device, that includes a battery management system, a method for effecting battery management, and a display of battery condition.

What is claimed is:

1. A method for battery management in a battery powered unit, said method comprising:
   monitoring the voltage level of a battery used to power an electrical unit the power output of which is battery voltage dependent; and
   repeatedly detecting a predetermined first low voltage level of said battery and, responsive to each detection of said predetermined first low voltage level, decrementing the power output of said electrical unit by a small amount relative to the power output then being provided to cause, so long as within the capability of said battery, said battery voltage to be maintained substantially at said predetermined first low voltage level.

2. The method of claim 1 wherein said method includes detecting a low voltage level higher than said first low voltage level and, responsive thereto, causing a warning indication to be made of said detected low battery voltage, and wherein said method also includes detecting a predetermined second low voltage level of said battery less than said predetermined first low level, and, responsive thereto, terminating operation of said unit.

3. The method of claim 1 wherein said method includes providing an indication of each decrementing of said power output of said unit.

4. The method of claim 1 wherein said method includes reducing said power output by no more than about one milliampere each time said power output is decremented.

5. The method of claim 1 wherein said method includes displaying an indication of needed battery replacement when said operation of said unit is terminated due to detection of a predetermined second low voltage level of said battery lower than that of said first predetermined voltage level.

6. The method of claim 1 wherein said step of detecting a predetermined first low level of said battery includes repeatedly checking said battery for low voltage and precluding decrementing of said power output unless said predetermined first low battery voltage is detected a preselected plurality of consecutive times.

7. The method of claim 6 wherein said step of repeatedly checking said battery for low voltage includes detecting of said predetermined first low battery voltage at least three consecutive times.

8. A method for battery management in a battery powered unit, said method comprising:
   monitoring the voltage level of a battery used to power an electrical unit the power output of which is battery voltage dependent;
   detecting a predetermined first low battery voltage and, responsive thereto, causing a warning indication to be made thereof; and
   repeatedly detecting a voltage lower than a predetermined second low battery voltage level and, responsive to each detection of said voltage lower than said predetermined second low battery voltage level, decrementing the power output of said electrical unit by a small amount relative to the power output then being provided to cause, so long as within the capability of the battery, said battery voltage to be maintained substantially at said second low voltage level.

9. The method of claim 8 wherein said method includes detecting a drop in said battery voltage to a third low voltage level less than that of said second low voltage level and, responsive thereto, terminating operation of said unit.

10. The method of claim 8 wherein said method includes providing a visual display as said warning indication of said detected first low battery voltage, and providing an audible sound indicative of each decrementing of said power output of said unit.

11. The method of claim 8 wherein said method include decrementing said power output by one of one milliampere and 0.39 milliamperes each time that the output power is decremented.

12. The method of claim 8 wherein said method includes detecting a low battery voltage level higher than said second low battery voltage level, and, responsive to each detection of said voltage higher than said second low battery voltage level, and with said power output then being at a rended level, incrementing said power output of said electrical unit to cause said battery voltage to be lowered to about that of said second low battery voltage level.

13. The method of claim 8 wherein said step of detecting a voltage lower than a predetermined second low battery voltage level includes repeatedly checking said battery for low voltage and precluding decrementing of said power output unless said second low voltage level of said battery is detected at least three consecutive times.

14. A battery powered electronic stimulating device, comprising:
   a battery supplying an output voltage;
   generating means for receiving said output voltage and generation a power output for stimulation purposes that is at least partially dependent upon said output voltage received from the battery; and
   control means connected with said battery for monitoring the voltage level of said battery and connected with said greeting means for controlling the power output thereof, said control means repeatedly detecting a first predetermined voltage level of said battery and, upon each detection of said first low voltage level of said battery, decrementing the power output of said electrical unit to cause said battery voltage to be maintained substantially at, so long as within the capability of said battery, said first low voltage level.

15. The device of claim 14 wherein said device include warning means for warning of detected low battery voltages.

16. The device of claim 15 wherein said warning means includes means for displaying a visual indicator indicative of at least one of detected low battery voltage and a need for battery replacement.

17. The device of claim 14 wherein said control means, upon detection of a low voltage level less than said first low voltage level, causes termination of operation said device.

18. The device of claim 14 wherein said control means, upon detection of a low battery voltage level higher than said first low battery voltage level, and with said power output then being at a reduced level, incrementing said power output of said device to cause said battery voltage to be lowered to about that of said first low voltage level.

19. The device of claim 14 wherein said control means includes a microprocessor.

* * * * *